(12) United States Patent
Strandemar

(10) Patent No.: US 9,984,447 B2
(45) Date of Patent: May 29, 2018

(54) GAS VISUALIZATION ARRANGEMENTS, DEVICES, AND METHODS

(71) Applicant: FLIR Systems AB, Taby (SE)

(72) Inventor: Katrin Strandemar, Rimbo (SE)

(73) Assignee: FLIR Systems AB, Täby (SE)

( * ) Notice: Subject to any disclaimer, the term of this patent is extended or adjusted under 35 U.S.C. 154(b) by 0 days. days.

(21) Appl. No.: 15/468,044

(22) Filed: Mar. 23, 2017

(65) Prior Publication Data

US 2017/0193645 A1 Jul. 6, 2017

Related U.S. Application Data

(63) Continuation of application No. 15/056,871, filed on Feb. 29, 2016, now Pat. No. 9,613,410, which is a
(Continued)

(30) Foreign Application Priority Data

Nov. 7, 2011 (EP) ..................................... 11188119

(51) Int. Cl.

| | |
|---|---|
| *G06T 5/10* | (2006.01) |
| *G06T 7/00* | (2017.01) |
| *G06T 11/00* | (2006.01) |
| *H04N 5/33* | (2006.01) |
| *G01N 21/3504* | (2014.01) |
| *G06T 5/50* | (2006.01) |
| *G06T 7/10* | (2017.01) |

(Continued)

(52) U.S. Cl.

CPC ........... *G06T 5/20* (2013.01); *G01N 21/3504* (2013.01); *G06T 5/10* (2013.01); *G06T 5/50* (2013.01); *G06T 7/0008* (2013.01); *G06T 7/13* (2017.01); *G06T 7/174* (2017.01); *G06T 11/001* (2013.01); *H04N 5/23293* (2013.01); *H04N 5/33* (2013.01); *H04N 5/332* (2013.01); *G06T 2207/10048* (2013.01); *G06T 2207/20056* (2013.01); *G06T 2207/20221* (2013.01); *G06T 2207/20224* (2013.01)

(58) Field of Classification Search

CPC ......... G06T 11/001; G06T 2207/10048; G06T 2207/20224; G06T 5/10; G06T 5/50; G06T 7/0085; G06T 7/0097

See application file for complete search history.

(56) References Cited

U.S. PATENT DOCUMENTS

| | | |
|---|---|---|
| 5,430,293 A | 7/1995 | Sato et al. |
| 5,656,813 A | 8/1997 | Moore et al. |
| | (Continued) | |

*Primary Examiner* — Gelek W Topgyal
(74) *Attorney, Agent, or Firm* — Haynes and Boone, LLP

(57) ABSTRACT

Gas visualization in an image depicting a scene, for an example embodiment comprises capturing a first IR image depicting the scene at a first time instance and a second IR image depicting the scene at a second time instance; performing image processing operations on image data derived from said first IR image and from said second IR image, to generate a collection of data representing the location of gas in one of the first or second IR images; and generating a third image by adjusting pixel values in an image depicting the scene, dependent on pixel values of said collection of data. According to various embodiments, there is further provided further processing of the collection of data, and/or gas detection, before generation of the third image with adjusted pixel values.

20 Claims, 7 Drawing Sheets

Related U.S. Application Data continuation of application No. 13/670,311, filed on Nov. 6, 2012, now Pat. No. 9,280,812.

(60) Provisional application No. 61/639,749, filed on Apr. 27, 2012.

(51) Int. Cl.
*H04N 5/232* (2006.01)
*G06T 5/20* (2006.01)
*G06T 7/13* (2017.01)
*G06T 7/174* (2017.01)

(56) References Cited

U.S. PATENT DOCUMENTS

| | | |
|---|---|---|
| 7,649,174 B2 | 1/2010 | Mammen et al. |
| 2002/0085768 A1 | 7/2002 | Yokose et al. |
| 2003/0025081 A1 | 2/2003 | Edner et al. |
| 2009/0200466 A1 | 8/2009 | Mammen et al. |
| 2009/0294666 A1 | 12/2009 | Hargel |
| 2010/0220193 A1 | 9/2010 | Hogasten et al. |
| 2010/0230593 A1 | 9/2010 | Hill, Jr. |
| 2010/0231722 A1 | 9/2010 | Hill et al. |
| 2010/0301214 A1 | 12/2010 | Jönsson |
| 2013/0250124 A1 | 9/2013 | Furry |
| 2013/0286213 A1 | 10/2013 | Cetin et al. |

GAS VISUALIZATION ARRANGEMENTS, DEVICES, AND METHODS

CROSS-REFERENCE TO RELATED APPLICATIONS

This application is a continuation of U.S. patent application Ser. No. 15/056,871, filed Feb. 29, 2016 and entitled "GAS VISUALIZATION ARRANGEMENTS, DEVICES, AND METHODS," which is hereby incorporated by reference in its entirety.

U.S. patent application Ser. No. 15/056,871, filed Feb. 29, 2016 is a continuation of U.S. patent application Ser. No. 13/670,311, filed Nov. 6, 2012 and entitled "GAS VISUALIZATION ARRANGEMENTS, DEVICES, AND METHODS," which is hereby incorporated by reference in its entirety.

U.S. patent application Ser. No. 13/670,311, filed Nov. 6, 2012 claims the benefit of and priority to U.S. Provisional Patent Application No. 61/639,749 filed Apr. 27, 2012 and to EP Patent Application No. 11188119.9 filed Nov. 7, 2011, which are incorporated herein by reference in their entirety.

TECHNICAL FIELD

Generally, embodiments of the invention relate to the technical field of gas visualization. More specifically, different embodiments of the application relates to gas visualization using an infrared (IR) imaging device.

BACKGROUND

Infrared (IR) imaging devices, such as IR cameras, can be used to find gas in various applications. For example, the IR camera manufacturer FUR has a cooled gas camera that is used for finding many different gases.

Detecting and visualizing gas using IR techniques can be difficult since IR imaging devices typically can detect and represent 65,000 thermal levels in a radiometric IR image but only have 255 colors to represent this data on the display. First, the gas detection in current prior art tends to be resource consuming with regard to processing power due to complicated operations required to detect gas present in an IR image. Secondly, the visualization of gas in an IR image also requires some kind of translation between the high resolution radiometric IR image and a displayed IR image. It is possible to work with level and span to visualize some smaller portion of these 65,000 levels onto the 255 color scale, this is however quite time consuming and it can be hard to adjust to the current gas present in an imaged scene. Furthermore, if there are large differences in temperature between objects in the imaged scene, pixels having relatively small temperature differences will be visualized as having the same color, or very similar colors. Thereby, the color difference between gas and surrounding pixels in the image may be non-existent or very small, meaning that it is not possible, or very hard, to discern the visualized gas in the image with the human eye.

Examples of related art are found in U.S. Pat. Nos. 5,656,813, 7,649,174, 5,656,813, and 7,649,174.

While the prior art is directed to gas detection, it is deficient because the conventional methods require too much computational power, do not provide accurate gas detection, and/or do not provide sufficient visualization of the detected gas.

Therefore, there is still a need for improvements in passive camera systems in order to increase the detection capability in terms of distinguishing between an infrared absorbing gas cloud and background elements as well as improved visualization in a computationally efficient matter.

SUMMARY

Embodiments of methods, arrangements and devices described herein provide techniques for performing improved visualization of gas present in an imaged or depicted scene. Furthermore, one or more embodiments provide improved and/or computationally inexpensive gas detection. For example, one or more embodiments may provide methods and apparatuses for improved gas detection and/or visualization using an IR imaging device. One or more embodiments may provide certain advantages over prior art techniques, such as to improve computationally efficient gas detection and/or visualization, enable detection of a small concentration of gas, enable detection of gas leaks (e.g., small or large gas leaks), provide easily interpretable visualization of gas, and/or enable an implementation that demands a relatively low computational effort.

In accordance with one or more embodiments, methods for gas detection and visualization in infrared (IR) image data depicting a scene comprise performing image processing operations on image data derived from a first IR image depicting the scene at a first time instance and from a second IR image depicting the scene at a second time instance, to generate a collection of data representing the location of gas in one of the first or second IR image; detecting gas within the scene by detecting gas representing pixels in the first or second IR image based on said collection of data; and generating a gas visualizing image by adjusting, in an image depicting the scene, pixel values of pixels corresponding to the gas representing pixels in one of said first or second IR image, such that the gas representing pixels are distinguishable in the gas visualizing image.

In accordance with one or more embodiments, arrangements and devices for gas detection and visualization in infrared (IR) image data depicting a scene comprise devices and functionality for performing image processing operations on image data derived from a first IR image depicting the scene at a first time instance and from a second IR image depicting the scene at a second time instance, to generate a collection of data representing the location of gas in one of the first or second IR image; detecting gas within the scene by detecting gas representing pixels in the first or second IR image based on said collection of data; and generating a gas visualizing image by adjusting, in an image depicting the scene, pixel values of pixels corresponding to the gas representing pixels in one of said first or second IR image, such that the gas representing pixels are distinguishable in the gas visualizing image.

For example, as in accordance with an embodiment, image processing methods are disclosed to generate a collection of gas representing data by generating a temporal difference image. According to different method embodiments, the difference image may be low-pass filtered and/or transformed into the frequency domain. These and other embodiment measures enable gas visualization as moving or transient elements stand out more clearly in a difference image, especially after low-pass filtering. Embodiments presented herein further enable gas detection by identifying moving or transient elements. Gas visualization according to embodiments is achieved by generating a gas visualizing image by adjusting the pixel values of gas representing pixels in an image depicting the scene such that the gas representing pixels are distinguishable with a high degree of processing efficiency.

In accordance with one or more embodiments, there is provided a computing system configured to process infrared (IR) image data, the computing system comprising a memory configured to store infrared image data depicting a scene and a processor configured to process infrared image data stored in the memory. The processor is further adapted to receive from the memory a first IR image depicting the scene captured at a first time instance; receive from the memory a second IR image depicting the scene captured at a second time instance; perform image processing operations on image data derived from the first and second IR images to generate a collection of data representing the location of gas in one of the first or second IR images; and generate a third image by adjusting pixel values, in an image depicting the scene, dependent on pixel values of the collection of data.

Other embodiments of the claimed invention relate to computer-readable mediums, and computer program products on which are stored non-transitory information for performing gas visualization and/or detection of gas present in an imaged or depicted scene.

The scope of the invention is defined by the claims, which are incorporated into this Summary by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF DRAWINGS

One or more embodiments of the present invention will be further explained based on various embodiments and with reference to the accompanying claims, in which:

Embodiments of the invention and their advantages are best understood by referring to the detailed description that follows. It should be appreciated that like reference numerals are used to identify like elements illustrated in one or more of the figures.

DETAILED DESCRIPTION

Introduction

Embodiments of the claimed invention relate to methods, IR imaging devices and/or IR imaging arrangements for performing gas detection and visualization of gas present in an imaged, or depicted, scene.

According to an embodiment, an IR imaging device is realized as a device wherein the units and functionality for performing, capturing, and processing of images are integrated in the device. An IR imaging device may for instance be realized as an IR camera. According to an embodiment, an IR imaging arrangement comprises one or more units and enables communication and/or transfer of data between the comprised one or more units for performing, capturing, and processing of images.

Other embodiments of the claimed invention relate to computer-readable mediums on which are stored non-transitory information for performing gas detection and visualization of gas present in an imaged, or depicted, scene.

The gas detection and visualization, for an embodiment, may be performed by identifying moving or transient elements, such as gas, in a captured IR image frame depicting a scene, by producing a temporal difference image; process the difference image in order to enable detection of gas; and generating a gas visualizing image by adjusting the pixel values of gas representing pixels in an image depicting the scene such that the gas representing pixels are distinguishable.

Figure 1:
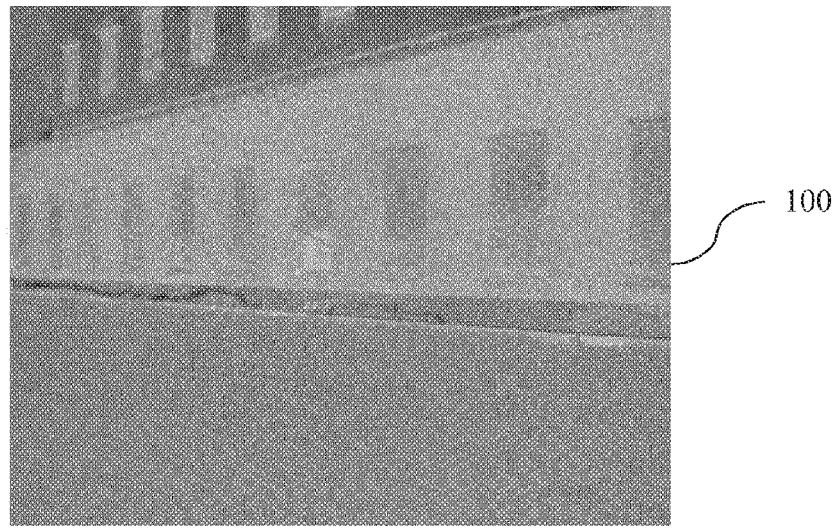
FIG. 1 shows an example of an IR image of a scene with a gas leak.

In FIG. 1, an example of an IR image 100 depicting a scene is shown, wherein there is a suspected gas leak. As generally known in the art, an IR image visualizes temperatures in a depicted scene. However, from this representation alone any gas present in the scene is typically not distinguishable, as illustrated in FIG. 1.

FIGS. 2A to 2D show an example of images in different steps of gas detection and visualization according to a method embodiment.

Figure 2A:
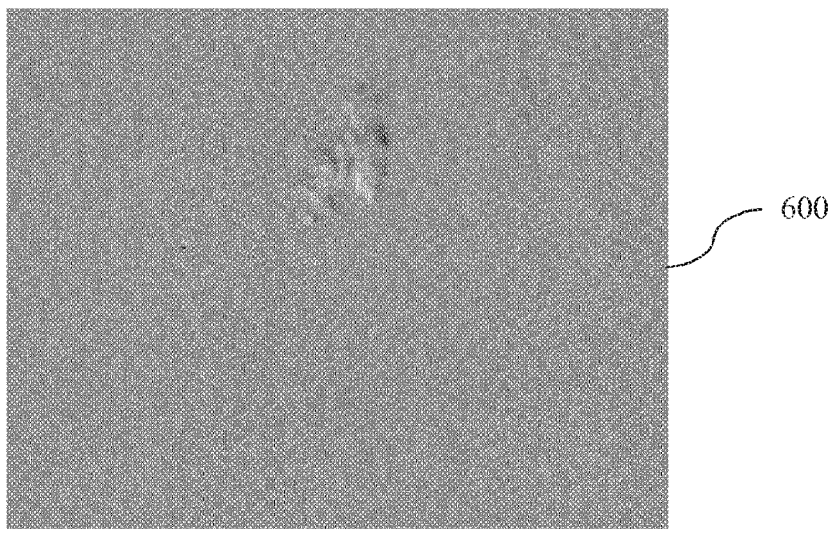
FIG. 2A shows an example of a processed temporal difference image based on a first and second IR image depicting the scene shown in FIG. 1, in accordance with an embodiment of the invention.

FIG. 2A shows an example of a processed temporal difference image 600 representing the difference between two IR image frames captured using the same IR imaging system at two different time instances. As can be seen in the figure, a gas formed entity is shown without any relation to the environment in the depicted scene.

Figure 2B:
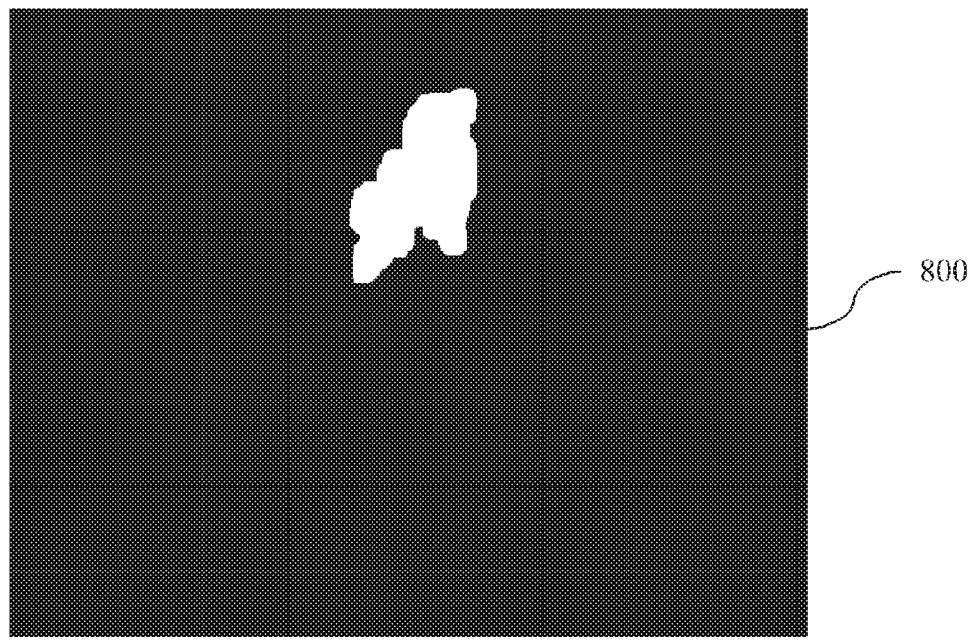
FIG. 2B shows an example of a gas map, also referred to as a gas image, here in the form of a binary gas map, or binary gas image, in accordance with an embodiment of the invention.

FIG. 2B shows an example of a gas map 800, also referred to as a gas image 800, wherein gas representing pixels in the IR image 100 of FIG. 1 have been detected and have been assigned values that distinguish the gas representing pixels from the remaining pixels. In the image 800 of FIG. 2B the gas representing pixels have all been assigned the value 1, or white, while the remaining pixels have all been assigned the value 0, or black, resulting in a binary gas map, or binary gas image. As will be further explained below, this binary gas map or binary gas image is used to improve processing efficiency.

Figure 2C:
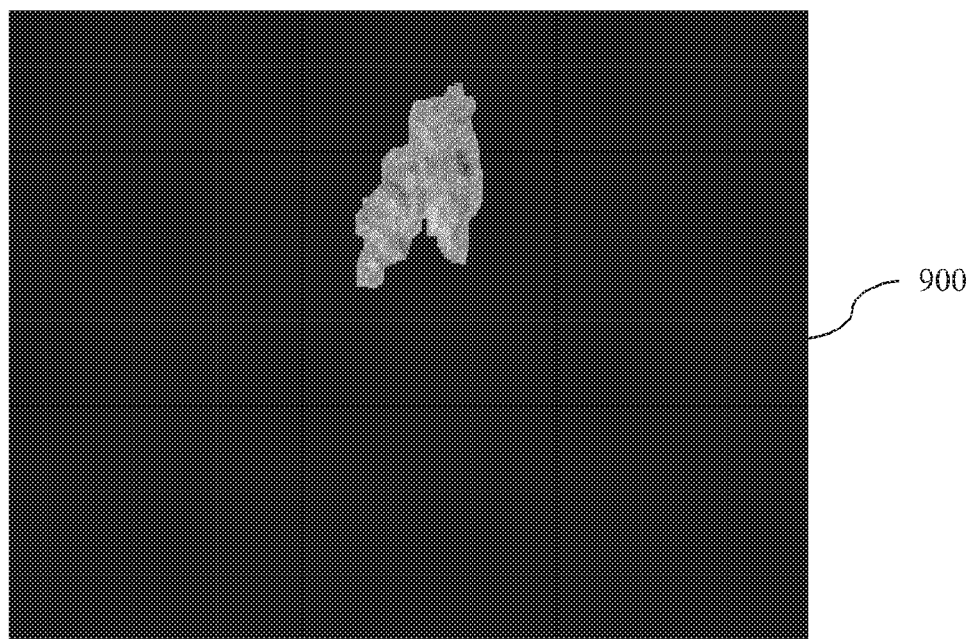
FIG. 2C shows an example of an intermediate gas image, in accordance with an embodiment of the invention.

FIG. 2C shows an example of an intermediate gas image 600, generated by combining the processed difference image 600 of FIG. 2A with the gas map 800, or gas image 800, of FIG. 2B.

Figure 2D:
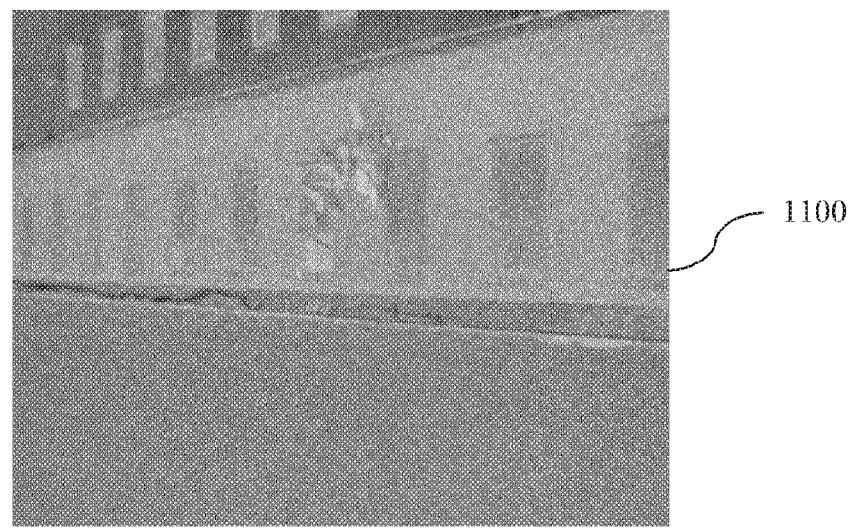
FIG. 2D shows an example of a gas visualization image, also referred to as a final gas image, in accordance with an embodiment of the invention.

FIG. 2D shows an image 1100 wherein the detected gas information is visualized, obtained through a combination of the IR image 100 of FIG. 1 and the intermediate gas image 800 of FIG. 2C. Such a combined image 1100, wherein the depicted scene is visualized and any gas present in the depicted scene is clearly visualized in relation to the depicted scene, will be presented in real time, or near real time, to the user or operator of the gas detection and visualization method, IR imaging device and/or IR imaging arrangement according to the embodiments described below.

Gas Detection and Visualization Method

Figure 3:
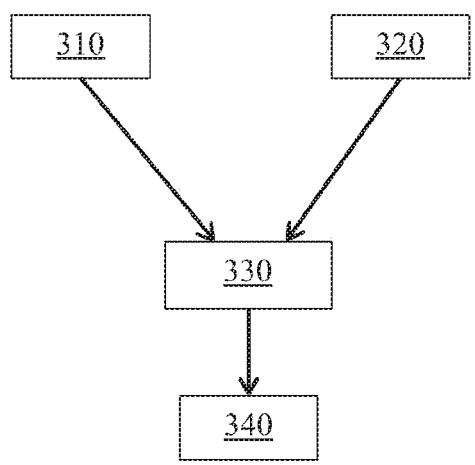
FIG. 3 shows a block diagram of a method, in accordance with an embodiment of the invention.

In FIG. 3, a block diagram schematically shows a general method according to an embodiment of the invention. This embodiment method for gas visualization in an image depicting a scene comprises:

In step S310: capturing a first IR image depicting the scene at a first time instance.

According to an embodiment, the captured first IR image is depicting a specified wavelength range within the infrared (IR) wavelength range.

In step S320: capturing a second IR image depicting the scene at a second time instance.

According to an embodiment, the captured second IR image is depicting the same wavelength range as the first IR image.

In different embodiment variants the captured first and second IR images may be intermediately stored in a data memory for later processing or may be transferred to and received in a data processor preferably in an IR imaging device or IR imaging arrangement in real time or close to real time. An exemplifying application in which these IR images are intermediately stored is when IR images are captured and collected using an IR imaging device at one time, whereas gas detection and gas visualization is performed later using functions according to embodiments of the invention implemented in the IR imaging device or IR imaging arrangement, or implemented in a separate analyzing software operable on a computer.

In step S330: performing image processing operations on image data derived from the first IR image depicting the scene at a first time instance and from the second IR images depicting the scene at a second time instance to generate a collection of data representing the location of gas in one of the first or second IR image.

According to an embodiment, the operations to generate a collection of data representing the location of gas comprise generating a temporal difference image based on the first IR image and the second IR image.

According to an embodiment, generating a collection of data representing the location of gas comprises further processing of the difference image before generating said third image. According to an embodiment, further processing of the difference image comprises transforming the difference image into the frequency domain, e.g. by a fast Fourier transform (FFT) operation or by a power spectral density (PSD) operation. According to another embodiment, processing of the difference image comprises low pass filtering of the collection of data.

According to an embodiment, the method further comprises stabilizing the first and second IR images before the temporal difference image is generated, either by stabilizing the first IR image with respect to the second IR image, or by stabilizing the second image with respect to the first IR image.

According to an embodiment, the image processing operations comprise detecting gas within the scene by detecting gas representing pixels in the first or second IR image of the previous step based on or dependent on the collection of data. According to an embodiment, the first and second IR images are stabilized before gas detection is performed. According to an embodiment, detecting gas within the scene comprises detecting gas representing pixels in the first or second IR image based on the difference image; and generating a third image or gas visualization image by adjusting, in an image depicting the scene, pixel values of pixels corresponding to the gas representing pixels in one of said first or second IR image, such that the gas representing pixels are distinguishable.

In step S340: generating a third image by adjusting pixel values in an image depicting the scene, dependent on pixel values of said collection of data.

According to an embodiment, generating a third image comprises adjusting pixel values in an image depicting the scene, dependent on a generated difference image, for instance by adding the difference image to the image depicting the scene. According to an embodiment, the difference image has previously been low-pass filtered in step S330.

According to an embodiment, the difference image or low-pass filtered difference image may further have been adjusted according to a predetermined color or grey scale palette, as described further below, before it is added to the image depicting the scene. According to an embodiment, the difference image may be multiplied by a factor, e.g. between 0 and 1, before it is added to the image depicting the scene, thereby adding information according to an opacity determined by said factor.

According to an embodiment, generating a third image comprises generating a gas visualizing image by adjusting in an image depicting the scene pixel values of pixels corresponding to the gas representing pixels in the first or second IR images of the previous step such that the gas representing pixels are distinguishable in the gas visualization image.

Gas Visualization Image and Gas Location Representing Data

There are different options for generating the gas visualization image. According to different embodiments, the image in which the pixel values of pixels corresponding to the detected gas representing pixels are adjusted such that the gas representing pixels are distinguishable is a selected IR image depicting the scene, captured using an IR imaging device comprised in the IR imaging device. This may for example be the first IR image or the second IR image of the above steps. Alternatively, it may be another selected IR image depicting the scene at some other time instance and preferably being captured by the same IR imaging system or IR detector as the mentioned first and second IR images. In another embodiment the gas visualizing image is generated based on a visual image, more specifically by adjusting, in a visual image depicting the scene, the pixel values of pixels corresponding to the detected gas representing pixels, the visual image having a predetermined relation to the first and second IR images and being captured using a visible light imaging system preferably comprised in an IR imaging device used to capture the mentioned first and second IR images.

When generating the gas visualization image it is practical to base the gas visualization image on a selected image depicting the scene and adjust only the pixel values of pixels corresponding to the detected gas representing pixels. Optionally, the gas visualization image may be generated by adjusting also pixels corresponding to the non-gas representing pixels based on image data of an image depicting the scene in order construct a suitably displayable image. This may for example be the case when a fusion image comprising IR image data and visual image data with detected gas visualized is generated as a gas visualization image. An important thing is in any case that the location of the gas is sufficiently accurately positioned in the depicted scene.

According to an embodiment, the collection of data representing the location of gas (i.e. gas location representing data) in the image comprises image pixel coordinates of image pixels representing gas. According to an embodiment, the collection of data has the form of a gas map, or gas image, wherein pixels having coordinates that coincide with the location of gas, in other words gas representing pixels, have pixel values that distinguish them from the remaining pixels. Different embodiments relating to such gas maps, or gas images, are presented below.

According to an embodiment, the image processing operations comprise creating a temporal difference image based on or derived from the first IR image and the second IR image, i.e. dependent on image data in the first IR image and the second IR image. According to an embodiment, gas present in the scene is made apparent by low-pass filtering the difference image, thereby removing noisy areas that may otherwise be interpreted as gas, for instance by a user viewing the difference image or in an optional gas detection step 412, described further below. According to an embodiment in which a combined image is generated, removal of noise from the difference image further gives the effect of avoiding that noise from being added to the combined image. The combined image is also referred to as third image or gas visualization image herein.

In further detail according to an embodiment, generating a gas visualizing image such that the gas representing pixels are distinguishable comprises selecting in the temporal difference image, pixels representing gas based on said collection of gas location representing data.

Embodiments of Gas Detection and Visualization

Figure 4A:
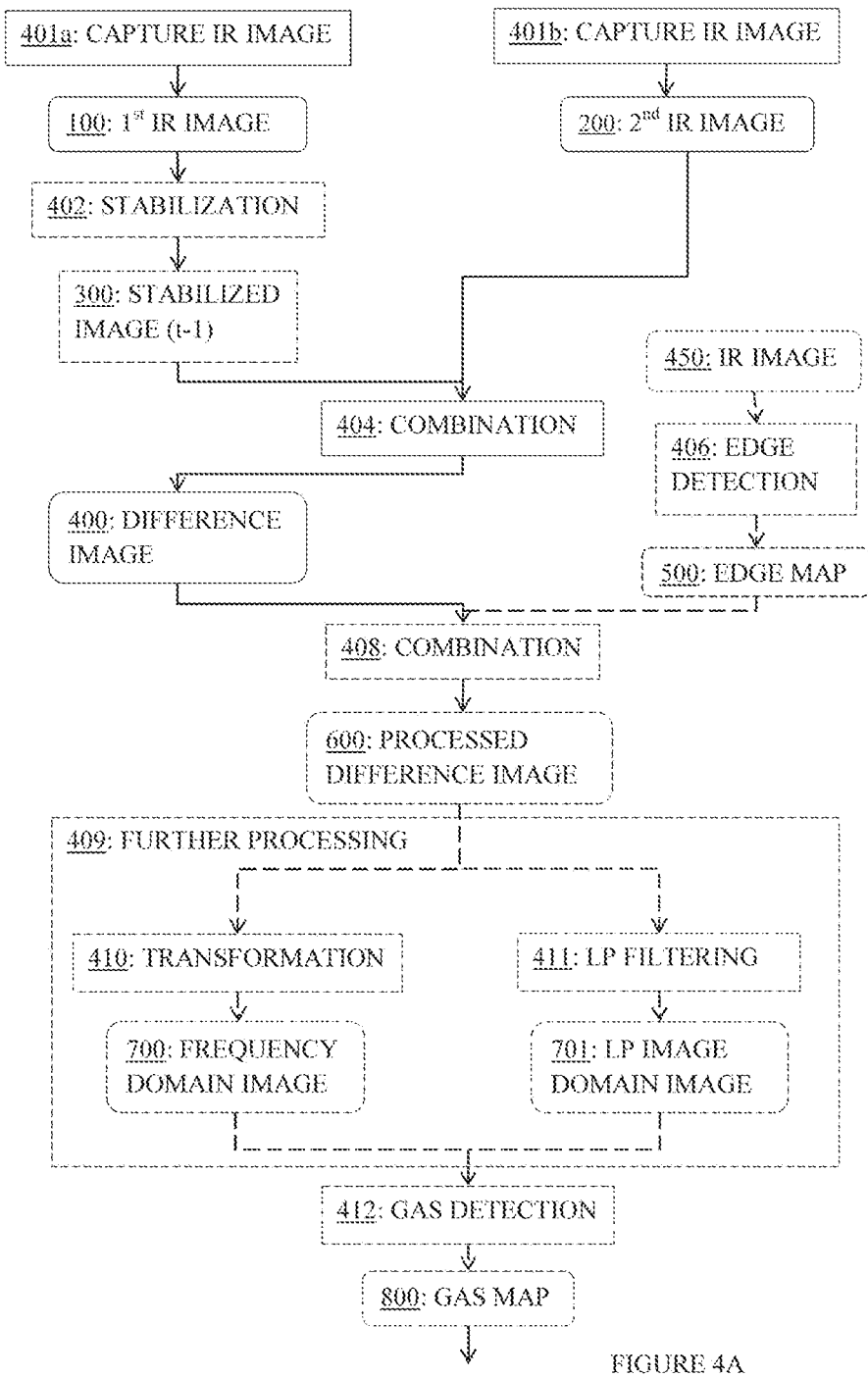
FIG. 4A shows of a block diagram of the first part of a method, in accordance with an embodiment of the invention.
Figure 4B:
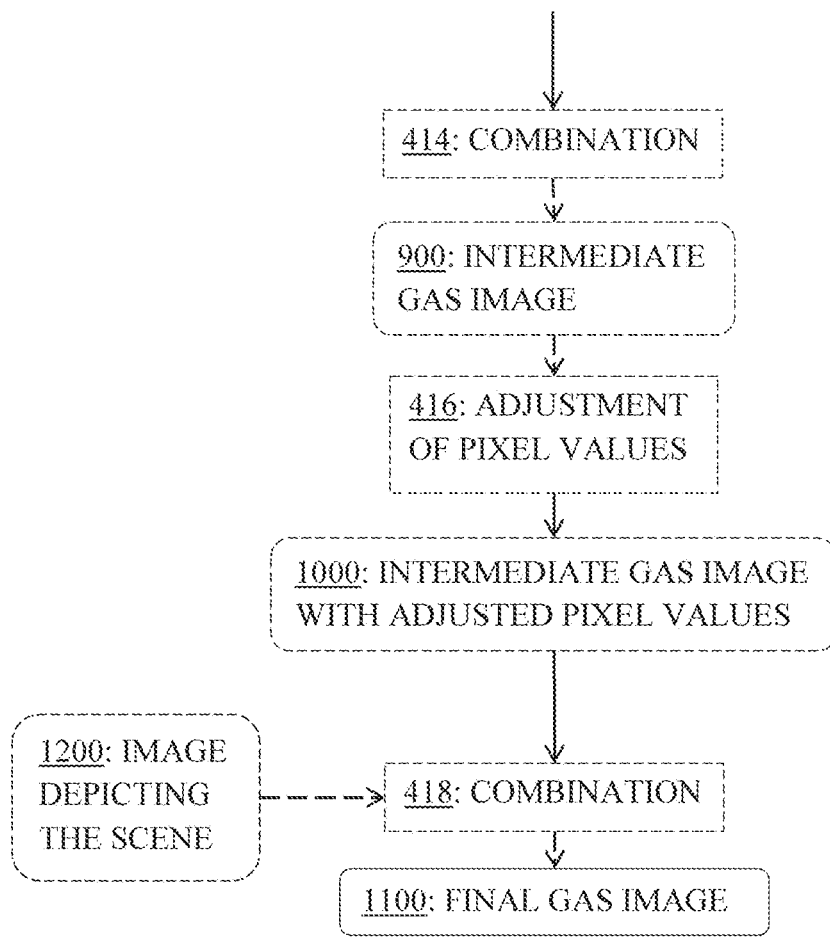
FIG. 4B shows a continuation of the method in FIG. 4A, in accordance with an embodiment of the invention.

FIGS. 4A and 4B show embodiments of the inventive gas detection and visualization method, wherein steps 401 to 412 relate mainly to gas detection, while steps 414 to 418 relate to visualization of the detected gas information.

In step 401*a* an IR image of the scene is captured, at a first time instance. The capturing results in a first ($1^{st}$) IR image 100. An example of such an IR image 100 is shown in FIG. 1.

In step 401*b* an IR image of the scene is captured from the same direction, i.e. with the same view, at a second time instance, preferably close in time to the first time instance and depicting the same wavelength range as the first IR image. The capturing results in a second ($2^{nd}$) IR image 200.

The first and second IR images are captured using the same IR imaging sensor, the IR imaging sensor being comprised in the IR imaging device.

The second IR image is also referred to as the current IR image, or current IR image frame, and is captured at the current time instance. The first IR image is also referred to as the previous IR image, or previous IR image frame, and is captured at a previous time instance, previous to the first time instance. According to an embodiment, the previous IR image and the current IR image are two subsequent IR image frames in an image frame sequence, captured at time instance (t−1) and (t), respectively. According to this embodiment, the IR imaging device may be an IR video camera adapted to capture a sequence of IR image frames.

The steps 402 to 412 relate to deriving image data from the first and second captured images and performing image processing operations on the image data derived from the first and second images to generate a collection of data representing the location of gas in the image. The collection of data may for instance be represented as an image or a map.

In an optional step 402 either the first IR image is stabilized with respect to the second IR image, or the second IR image is stabilized with respect to the first IR image, to compensate for movements of the IR imaging device etc. The stabilization is preferably performed before the temporal image is generated.

Different ways of accomplishing image stabilization are well known in the art, and may be roughly divided into: optical image stabilization methods, wherein one or more physical optical element, e.g. lens, sensor, detector, is moved to compensate for the motion of the imaging device; and digital image stabilization, wherein the electronic image is shifted from frame to frame in order to compensate for the motion of the imaging device, based on detected movements of e.g. pixels or objects identified in the images. Image stabilization systems are commonly used in visual imaging devices in order to compensate for movements of the imaging device.

Stabilization reasons and options are further explained below, in connection with step 404.

In step 404, a temporal difference image 400 is generated, based on, or derived from, the first IR image and the second IR image. In other words, the first and second IR images are combined in such a way that a temporal difference image 400 is obtained.

The combination may for instance consist in subtracting the first image from the second image, or to subtract the second image from the first image, thereby obtaining an image representing the difference between the compared images. Since the difference image will comprise information on changes between the first and second IR image frames, moving elements will be visible in the difference image. Moving elements in this context may for instance be transient elements, such as gas.

In order to obtain a good difference image, the photometric values of two images used for generating a difference image must be compatible. Since the first and second IR images, depicting a real world scene, both represent the infrared spectrum of light, their photometric values are compatible.

Furthermore, it is advantageous if the two images are aligned, or registered, so that corresponding pixels coincide. Therefore, the compared first and a second IR image are captured in close succession, and by the same IR imaging sensor. Preferably, the two images are two successive image frames in an image frame sequence. The reason for capturing the images in close succession to each other is that the real world scene will not have changed much from the first image frame to the second and the second image thereby comprises substantially the same scene as the first image, with minor differences caused by movements of objects in the imaged scene, movements of the IR imaging device or random noise. As can be readily understood by a person skilled in the aft, a first and a second image frames captured at time instances far apart may be used for the methods described herein and provide a good result as long as the real world scene will not have changed much from the first image frame to the second and the second image thereby comprises substantially the same scene as the first image, and as long as the IR imaging device has not moved to much in relation to the imaged scene. This may for instance be true for a monitoring situation wherein monitoring is performed over time with a camera fixedly mounted or placed on a stand, or tripod, in front of the imaged scene. By subtracting the first image from the second image, or the second image from the first image, a difference image is obtained, comprising the differences caused by movements of objects in the imaged scene, movements of the imaging device and/or random noise.

In the difference image all differences caused by movements of objects in the imaged scene will be comprised, meaning that even information on very small concentrations of gas, such as very small gas leaks, will be comprised in the difference image.

High spatial frequency content, representing edges and contours of the objects in the scene, may appear in a difference image unless the imaged scene is perfectly unchanged from the first time instance to the second, and the imaging device, and consequently also the imaging sensor, has been kept perfectly still. The scene may for example have changed from one frame to the next due to changes in light in the imaged scene or movements of depicted objects. Also, in almost every case the imaging device and sensor will not have been kept perfectly still, meaning that all stationary or non-moving parts of the imaged scene will not appear in the same location in the first and the second IR image. If the imaging device is handheld, it is evident that there will be movements caused by the user of the imaging device. If the imaging device is stationary, for example on a stand, vibrations of the imaging device or the surroundings may cause movements of the imaging sensor. Therefore, it may be advantageous to perform the optional image stabilization of step 402 before generating the temporal difference image 400.

Reducing Irrelevant Information by Edge Detection and Removal

In an optional step 406, edge detection is performed on the difference image, resulting in a data collection comprising edge location information, i.e. information on where edges are located in the difference image. The data collection comprising edge location information may be in the form of an edge map 500, also referred to as an edge image 500.

The optional edge detection may be performed according to any method known in the art, for instance comprising search-based methods, such as searching for local directional maxima of the gradient magnitude, and/or zero-crossing based methods, such as searching for zero crossings in a second-order derivative expression, usually the zero-crossings of the Laplacian or the zero-crossings of a non-linear differential expression. Edge detection according to the above methods may also comprise image smoothing as a preprocessing step, for instance low-pass filtering or Gaussian smoothing, per se known in the art.

Figure 5:
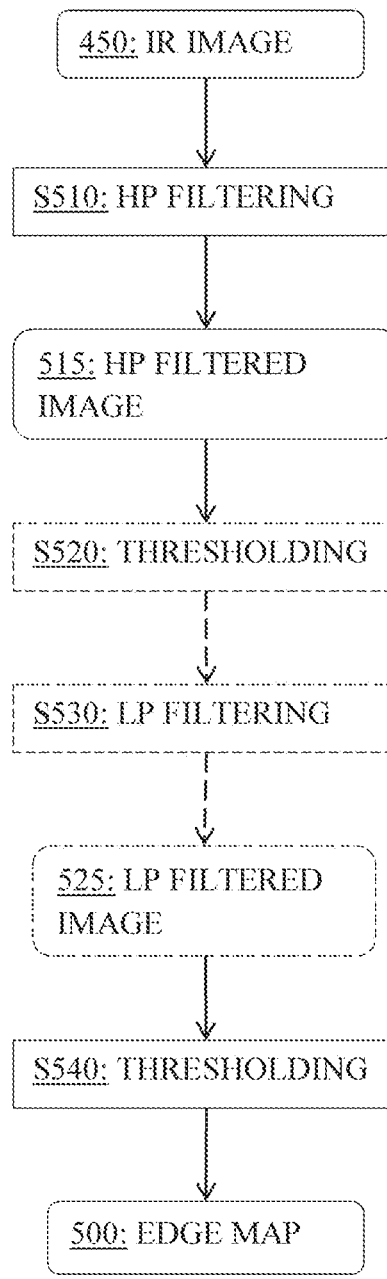
FIG. 5 shows a block diagram of an edge detection method, in accordance with an embodiment of the invention.

In FIG. 5, an embodiment of an edge detection method is shown, wherein edges are detected in an IR image 450. According to alternative embodiments, the IR image 450 is the first IR image 100; the second IR image 200, or another IR image captured using the same IR imaging device as has been used to capture the first and second IR images. According to another embodiment, the IR image 450 is the difference image 400. However, using the difference image 400 introduces the risk that gas information is wrongfully detected as edges and therefore removed from the difference image.

In step S510, a high pass (HP) filter is applied to the IR image 450. Thereby, high frequency content in the IR image such as edge information is detected, for example based on identification of local directional maxima of the gradient magnitude. From the HP filtering as HP filtered image 515 is obtained. As described above, any suitable method may be used to obtain edge information from an image, HP filtering being one common example.

In an optional step S520, a threshold is applied to the HP filtered image. From the optional threshold operation, a binary HP filtered image is obtained wherein all pixels comprising the detected high frequency content are assigned a first pixel values while the remaining pixels are assigned a second value.

According to different embodiments, the threshold level is preset in production or calibration of the IR imaging device. Typically, the threshold value depends on the general noise level in the images captured by the IR imaging system of the IR imaging device or IR imaging arrangement, and the threshold value is set such that as few noise representing pixels as possible will be wrongfully detected as gas, while the sensitivity for gas detection is as high as possible so that no gas pixels are missed in the gas detection.

According to an embodiment, sensitivity for gas detection may be adjusted by an operator of the IR imaging device, using interaction functionality of the IR imaging device.

In the resulting HP filtered image 515, or the binary HP filtered image if the optional step S520 has been performed, typically contains noise. In order to remove the noise, the HP filtered image S151, or the binary HP filtered image, may be low pass (LP) filtered in optional step S530.

According to an embodiment, LP filtering is performed using an LP kernel, wherein the kernel values are adapted such that the LP filtering leads to expansion of the detected edges and removal of noise in the form of individual pixels, or a cluster of few pixels, comprised in the image.

In general, a kernel filter works by applying a kernel matrix to every pixel in the image. The kernel contains multiplication factors to be applied to the pixel and its neighbors and once all the values have been multiplied, the pixel value is replaced with for instance the sum of the products, or a mean value of the sum of the products. By choosing different kernels, different types of filtering can be applied, as is well known in the art.

For instance, the kernel may be a matrix of 3*3, 5*5, 7*7, 9*9, or any other suitable size, and value of the kernel center pixel may be larger than the value of the remaining kernel pixels. By means of example only, the kernel may have a center pixel value of 8 and remaining pixel values set to 1. Any other suitable values may however be used as well as any selected weighting between different parts of the kernel meaning that all pixels that are not the center pixel do not need to have the same pixel value.

According to an embodiment, the LP filter kernel is applied to each pixel of the HP filtered image 515, or the binary HP filtered image, whereby the pixel value is set to the sum of the all of the pixel values of the HP filtered image 515, or the binary HP filtered image, multiplied/weighted by the values of the applied kernel. Alternatively, the pixel value is set to a mean value of obtained by dividing said sum with the number of pixels in the applied kernel.

The different LP filtering embodiments all lead to the filtered pixels being assigned a new pixel value taking into account the values of the surrounding pixels in the original image. Thereby, a pixel that originally has been set to a value indicating that it does not contain edge information in the HP filtered image 515, or the binary HP filtered image, may through the LP filtering be set to a value that indicates that it does contain edge information if a significant amount of the surrounding pixels have values indicating that they contain edge information. A significant amount of the surrounding pixels may for instance be 50% of the surrounding pixels, two thirds of the surrounding pixels, or any other suitable fraction. This results in edge expansion, as continuous edge information is enhanced in the image when pixels surrounding detected edges are included in the detected edges. This expanding of the detected edges is thus performed before generating a processed difference image as explained below.

On the other hand, a pixel that originally has been set to a value indicating that it contains edge information in the HP filtered image 515, or the binary HP filtered image, may through the LP filtering be set to a value that indicates that it does not contain edge information if a significant amount of the surrounding pixels have values indicating that they do not contain edge information. A significant amount of the surrounding pixels may for instance be 50% of the surrounding pixels, two thirds of the surrounding pixels, or any other suitable fraction. This results in removal of noise in the form of individual or few pixels that are wrongfully detected as containing edge information since edges detectable in images consist of a number of subsequent pixels extending in a defined direction.

Through the LP optional filtering of step S530, an LP filtered image 525 is generated.

In step S540, a threshold is applied to the LP filtered image 525, resulting in the generation of an edge map 500, also referred to as an edge image 500.

According to an embodiment, pixels that have values above the threshold value are identified as representing edge information while the remaining pixels are not identified as representing edge information.

According to an alternative embodiment, pixels that have values under the threshold value are identified as representing edge information while the remaining pixels are not identified as representing edge information.

According to an embodiment, the edge map 500, or edge image 500, wherein the pixels that have been identified as representing edge information, i.e. comprising the detected edge information, are assigned pixel values that differ from the pixel values of the remaining pixels. Alternatively, the remaining pixels are assigned pixel values that differ from the pixel values of the pixels that have been identified as representing edge information, i.e. comprising the detected edge information.

According to another embodiment, the pixels that have been identified as representing edge information, i.e. comprising the detected edge information, are assigned a first pixel value and the remaining pixels are assigned a second pixel value. Optionally, the resulting edge map, or edge image, is a binary map, or binary image, wherein pixels representing detected edge information are assigned the pixel value 1 and the remaining pixels are assigned the pixel value 0, or wherein pixels representing detected edge information are assigned the pixel value 0 and the remaining pixels are assigned the pixel value 1.

According to another embodiment, the pixels that have been identified as representing edge information, i.e. comprising the detected edge information, are assigned a pixel value, for instance 1 or 0, while the pixel values of the remaining pixels are left unchanged. Alternatively, the remaining pixels are assigned a pixel value, for instance 1 or 0, while the pixel values of pixels that have been identified as representing edge information, i.e. comprising the detected edge information, are left unchanged.

Thereafter, in an optional step 408, a processed difference image is generated by combining the edge map, or edge image, 500 with the difference image 400 such that the detected edge information is removed.

For instance, if the edge map, or edge image, is a binary map, or binary image, wherein pixels representing detected edge information have been assigned the pixel value 0 and the remaining pixels have been assigned the pixel value 1, then the edge map or binary image may be multiplied with the difference image in order to obtain a processed difference image 600, wherein the edge information has been removed.

Alternatively, if the edge map, or edge image, is a binary map or binary image wherein the edge representing pixels have been assigned the pixel value 1 and the remaining pixels, i.e. pixels that have not been identified as representing edges, have been assigned the pixel value 0, then the gas map or binary image may be subtracted from the difference image, followed by a step wherein all pixels values <0 are set to 0, in order to obtain a processed difference image 600, wherein the edge information has been removed.

An example of such a processed difference image 600, wherein edges have been detected and removed, is shown in FIG. 2A.

As can be seen in FIG. 2A, only elements that differ between the first and second IR image frames, such as transient elements, that further have not been detected as edges remain in the processed difference image. In the processed difference image 600 of FIG. 2A, only transient elements in the form of a gas cloud remain, clearly showing the image location of gas detected in the depicted scene.

As stated above, steps 406 and 408 are optional, but are shown to further improves the gas visualization performance since unwanted elements present in the difference image, i.e. elements that are not likely to represent gas, are removed and therefore will not be emphasized by the visualization method in the final gas image obtained in step 418 below. The edge detection and removal steps are especially advantageous to include in images depicting scenes comprising strait lines, for instance outlines of buildings, walls, floors, roofs, streets, pipes, any rectangular or cylindrical objects or constructions, and so on. Therefore, it would typically be advantageous to include the edge detection and removal steps when the aim is to detect gas during building, construction, pipe, street or city inspections.

If the optional steps 406 and 408 have been performed, the processed difference image is used as input to the transformation in the next step, step 410, and consequently the processed difference image is the basis of the remaining steps presented in FIGS. 4A and 4B.

Further Processing of Difference Image

Steps 409 and 412 of FIG. 4A below are optional.

According to an embodiment, in Step 409 further processing of the difference image, or processed difference image, is performed. In other words, the operations to generate a collection of data representing the location of gas comprises further processing of the difference image before generating the resulting gas visualization image, also referred to as the third image in connection with FIG. 3. According to embodiments presented below, the further processing of step 409 may comprise transforming the collection of data into the frequency domain in an optional step 410 by: an FFT operation; or a PSD operation. Alternatively, according to embodiments presented below, the further processing of step 409 may comprise low pass filtering the collection of data in an optional step 411. According to an embodiment, a combination of steps 410 and 411 may be performed.

According to an embodiment, low pass (LP) filtering of the collection of data, in other words difference image 400 or processed difference image 600, is performed in step 411, resulting in a low pass (LP) image 701. By low pass filtering the difference image 400 or processed difference image 600, noise present in the image 400, 600 is removed or reduced. Thereby any gas present in the scene becomes more clearly distinguishable as unnecessary and disturbing information, in the form of noise, is no longer present in the image.

According to an embodiment, step 410 is performed. In the transforming step 410, the difference image 400, or the processed difference image 600 if the optional steps 406 and 408 have been performed, is transformed from the time domain into the frequency domain. Gas detection is then performed in the transformed difference image to identify pixel coordinates of pixels representing gas present in the scene. Hereinafter, the phrase difference image will be used in the text, referring to either one of the difference image 400, or the processed difference image 600.

The transformation is performed by an operation according to a predetermined transformation function, typically a Fourier transform such as a fast Fourier transform (FFT, FFT$_2$), or a transform based on a Fourier transform, such as a discrete cosine transform (DCT) or a power spectral density (PSD), which describes how the power of a signal or time series is distributed with frequency. The inventor has found that a Fourier transformation of the image into the frequency domain makes the frequencies of the gas present in the image appear surprisingly well.

According to an embodiment, a PSD estimate is calculated using a per se known Welch method described in Stoica et al., "Introduction to spectral analysis" (Prentice Hall, 1997), wherein data segments are allowed to overlap and can be represented as $$x_i(n) = x(n + iD) \quad \text{(Eq. 1)}$$
$$\begin{cases} n = 0, 1, \ldots, M-1 \\ i = 0, 1, \ldots, L-1 \end{cases}$$

where the starting point for segment i is iD and the segment length is M. According to an embodiment M>D, meaning that there will be overlap, e.g. M=D2 corresponds to an overlap of 50%. The total length of the signal is LD.

According to an embodiment, the $i^{th}$ periodogram is calculated as $$\hat{X}^{(i)}(f) = \frac{1}{MU} \left| \sum_{n=0}^{M-1} x_{i(n)w(n)} e^{-j2\pi fn} \right|^2 \quad \text{(Eq. 2)}$$
$$i = 0, 1, \ldots, L-1$$

Where U is a normalization factor that corresponds to the power in the window function, given by:

$$U = \frac{1}{M} \sum_{n=0}^{M-1} w^2(n) \quad \text{(Eq. 3)}$$

The Welch power spectrum $\hat{X}(f)$ is then defined as the average of the periodograms in Eq. 2, i.e., $$\hat{X}(f) = \frac{1}{L} \sum_{i=0}^{L-1} X^{(i)}(f) \quad \text{(Eq. 4)}$$

According to an embodiment, a Hamming window function defined as $$w(n) = 0.54 - 0.46 \cos\frac{2\pi n}{M-1} \quad \text{(Eq. 5)}$$

$$0 \leq n \leq \leq M-1$$

is used together with a 50% overlap for the PSD estimates. As is readily apparent to a person skilled in the art, different window functions and different amounts of overlap may be applied according to circumstances.

According to an embodiment, the transformation of the difference image into the frequency domain is performed block wise for difference image blocks of a predetermined size, using image blocks of a size smaller than the size of the difference image. By means of example, the block size may be 2*2, 4*4, 8*8, 16*16, 32*32 or 32*24 pixels. Any suitable block size may be chosen depending on circumstances, e.g. dependent on the size of the difference image onto which the transform is applied. Generally it is advantageous to use blocks that are not too small in order for low frequency information to be included and detectable within the block.

According to an embodiment, the block may be converted into an array, wherein the rows of the matrix are placed one after another. Thereafter, the resulting signal, in array format, is used for the subsequent frequency transformation.

Optionally, the block wise transformation into the frequency domain is not performed for every pixel in the difference image, but instead is performed for a sub portion of the pixels of the difference image. Thereby, the transformation may also result in a down sampling of the difference image, resulting in a down sampled frequency domain image 700, i.e. frequency domain representation of the difference image. For example, a frequency transformation may be performed for every tenth pixel, meaning that the resulting frequency domain image 700 is down sampled ten times.

If a down sampling has taken place during the frequency transformation step the signal, i.e. the frequency domain image 700, is up-sampled to its original size again after the frequency transformation. According to different embodiments the up-sampling may be performed using any kind of interpolation method per se known in the art, such as for instance nearest neighbor interpolation, linear interpolation, bilinear interpolation, polynomial interpolation, cubic interpolation, spline interpolation, or cubic spline interpolation.

As is readily apparent to a person skilled in the aft, any down sampling factor may be selected dependent on circumstances. If the main aim is to maintain as much information as possible in the transformation step, the block wise transformation may be performed for every pixel, every other pixel or every third pixel, for example. If on the other hand the aim is to reduce information in order to obtain computational efficiency when performing further calculations on the frequency domain image 700, a larger sampling distance may be selected, for instance resulting in frequency transformation of every tenth, twentieth or thirtieth pixel. Evidently, the selection of down sampling factor also depends on the size of the difference image, i.e. how much information the difference image contains before the transformation. As is readily apparent to a person skilled in the art a pixel wise transformation is possible, wherein no down- and up-sampling is necessary, but it will be more computationally expensive.

For a specified IR imaging device having specified IR optics, the size of the IR images, and thereby the size of the difference image, are typically known. Therefore, an appropriate down sampling factor may be preset during production or calibration of the imaging device, or preselected by a user. According to an embodiment, the down sampling factor is selected by the user and manually input into the IR imaging device during use.

According to an embodiment, each pixel is assigned the value of a selection of the largest frequency peak, the largest peak within the low frequency content or a peak in the low frequency content within the corresponding transformed image block related to the pixel. According to another embodiment, each pixel is assigned the value of the added pixel value of two or more such peaks.

Gas Detection in Transformed Difference Image

Step 412 is optional and comprises further processing of the difference image 400, or a processed version of the difference image in the form of a processed difference image 600, frequency domain image 700 or LP image 701. Below, the term difference image may refer to any of the images 400, 600, 700 or 701.

According to an embodiment, step 412 comprises detecting gas within the scene by detecting gas representing pixels in the first IR image 100 or second IR image 200 based on the difference image 400, 600, 700, 701; and generating a third image, or final gas image 1100, by adjusting, in an image depicting the scene, pixel values of pixels corresponding to the gas representing pixels in one of said first or second IR image 100, 200, such that the gas representing pixels are distinguishable.

According to an embodiment, in step 412, gas detection is performed in the transformed difference image, also referred to as the frequency domain image 700. According to another embodiment, in step 412, gas detection is performed in the LP image 701.

According to an embodiment, the gas detection is performed in the difference image 400, 600, 700, 701 in order to identify the location of pixels representing transient elements, such as gas, present in the depicted scene. The location of pixels may typically be represented as the coordinates of the pixels in the difference image 400, 600, 700, 701.

According to an embodiment, the location of pixels representing gas present in the depicted scene is detected by LP filtering or thresholding the difference image 400, 600, 700, 701 according to a LP filtering or threshold value, separating the gas representing image pixels from the non-gas representing image pixels based on the difference image 400, 600, 700, 701 pixel values.

As part of the gas detection step, low-pass filtering or thresholding the pixels of the difference image 400, 600, 700, 701 may in one embodiment be used to generate a collection of data representing the location of gas in one of the IR images to create or generate a gas map, or a gas image 800 wherein the pixels that have been identified as representing gas information, i.e. comprising the detected gas information, are assigned pixel values that differ from the pixel values of the remaining pixels. Alternatively, the remaining pixels are assigned pixel values that differ from the pixel values of the pixels that have been identified as representing gas information, i.e. comprising the detected gas information.

According to another embodiment, the pixels that have been identified as representing gas information, i.e. comprising the detected gas information, are assigned a first pixel value and the remaining pixels are assigned a second pixel value. Optionally, the resulting gas map, or gas image, is a binary map or image wherein pixels representing detected gas information are assigned the pixel value 1 and the remaining pixels are assigned the pixel value 0, or wherein pixels representing detected gas information are assigned the pixel value 0 and the remaining pixels are assigned the pixel value 1.

According to another embodiment, the pixels that have been identified as representing gas information, i.e. comprising the detected gas information, are assigned a pixel value, for instance 1 or 0, while the pixel values of the remaining pixels are left unchanged. Alternatively, the remaining pixels are assigned a pixel value, for instance 1 or 0, while the pixel values of pixels that have been identified as representing gas information, i.e. comprising the detected gas information, are left unchanged.

Gas Detection and/or Visualization Modes

According to an embodiment, combination of embodiments according to the further processing of steps 410, 411 and 412 represent different modes available in an IR imaging device or IR imaging arrangement. In other words, there are more than one mode for further processing, comprising a selection of transforming the collection of data into the frequency domain by use of an FFT operation or a PSD operation; low pass filtering the collection of data; and/or performing gas detection.

According to an embodiment a user of an IR imaging device or IR imaging arrangement is enabled to select a mode, or switch between modes, using for instance interaction functionality 4 described below in connection with FIG. 6. According to an embodiment, selectable modes are presented to a user as menu options in a graphical user interface on a display integrated in or coupled to the IR imaging device. According to an embodiment, a mode is automatically selected in production, calibration or during use, dependent on circumstances.

According to a use case embodiment, it may be beneficial to use a mode comprising transforming the collection of data into the frequency domain by use of an FFT operation or a PSD operation and gas detection according to methods described above for an IR imaging device that is more or less stationary. This may for instance be true for a monitoring type camera that is fixedly mounted, or for a camera placed on a stand, or tripod. However, this mode may of course be used also for a handheld IR imaging device.

According to another use case embodiment, it may be beneficial to use a mode comprising low pass filtering, and optionally also gas detection comprising thresholding, for a handheld camera that is likely to move over time, relative to the imaged scene. The gas detection and/or visualization will in this case often not be as exact as in the mode described above. However, this mode still provides a greatly enhanced image with regard to visualization of gas, as compared to an image wherein no further processing has been performed. However, this mode may of course also be used in a monitoring situation wherein the IR imaging device is fixedly mounted or placed on a stand, or tripod.

According to an embodiment, if no specific mode has been selected, by a user or automatically dependent on circumstances, the display integrated in or coupled to the IR imaging device displays a regular IR, visual light or combined image that has not been processed according to embodiments described herein.

Generating Gas Visualization Image

Steps 414 to 418 relate to generating a gas visualizing image by adjusting the pixel values of gas representing pixels in an image depicting the scene, such that the gas representing pixels are distinguishable.

Step 414 is optional and may be performed if step 412 has been performed.

According to an embodiment, in step 414, an intermediate gas image 900 is generated by combining the gas map, or gas image, 800 with the difference image such that pixels corresponding to the pixels that have been identified as representing gas information, i.e. having been assigned one or more gas identifying values in the gas map, or gas image, are assigned the pixel values of the corresponding pixels in the difference image. The pixel values of the remaining pixels in the intermediate gas image 900 are for instance set to 0, 1 or any other value selected to clearly separate or distinguish the remaining pixels from the pixels corresponding to the pixels that have been identified as representing gas information. This results in the intermediate gas image 900 being a processed version of the difference image, wherein all pixel information from the difference image regarding the pixels that have been identified as representing gas information is maintained, while all pixel information from the difference image regarding the remaining pixels is removed, e.g. by assigning all remaining pixels to a single pixel value that is not dependent on the difference image.

For instance, if the gas map, or gas image, is a binary map or image wherein the gas representing pixels have been assigned the pixel value 1 and the remaining pixels, i.e. pixels that have not been identified as representing gas, have been assigned the pixel value 0, then the gas map or image may be multiplied with the difference image in order to obtain a processed difference image, wherein the non-gas pixel information is removed.

Alternatively, if the gas map, or gas image, is a binary map or image wherein the gas representing pixels have been assigned the pixel value 0 and the remaining pixels, i.e. pixels that have not been identified as representing gas, are assigned the pixel value 1, then the gas map or image may be subtracted from the difference image, followed by a step wherein all pixels values <0 are set to 0.

An example of an intermediate gas image 900, wherein pixels representing gas have been detected and assigned the pixel values of the corresponding pixels in the difference image, and further wherein pixel information for all non-gas pixels has been removed, is shown in FIG. 2C.

In an optional step 416, the pixel values of the image input from the previously performed step are adjusted.

According to an embodiment, the input image is a generated difference image 400, 600 or LP image 701, and adjusting the pixel values comprises adjustment according to a predetermined color or grey scale palette, as described further below.

According to an embodiment, an intermediate gas image with adjusted pixel values 1000 is generated. According to an embodiment, the pixel values of the gas representing pixels in the intermediate gas image 900 are adjusted according to a predetermined palette of pixel values, to generate an intermediate gas image with adjusted pixel values 1000.

The predetermined palette may comprise any appropriate selection of representations distinguishable from each other to the human eye, for instance grey scale values, different intensity values, different patterns such as halftone patterns, different shades of a certain color such as red, green or blue, or a scale comprising two three, or more different colors of different hue, saturation or intensities. As is readily apparent to a person skilled in the art, the palette may comprise a single pixel value, such as a single color value with no variation in hue, saturation or lightness/intensity, resulting in a flat color representation when applied to the pixel values of the gas representing pixels in the intermediate gas image 900.

Regardless of which representations are selected for the palette, the representations in the selected palette are mapped to the pixel values of the intermediate gas image goo, such that a certain pixel will be represented by a certain pixel value according to the selected palette. According to an embodiment the mapping relationships are predetermined, for example during production or calibration the IR imaging device, or during the development or implementation of the gas detection and visualization method.

After adjustment of the pixel values in an intermediate gas image goo, an intermediate gas image with adjusted pixel values 1000 is thus obtained.

In step 418 a gas visualization image, also referred to as a final gas image 1100, is generated.

According to an embodiment, the final gas image 1100 is generated by adjusting the pixel values of gas representing pixels in an image depicting the scene 1200, such that the gas representing pixels are distinguishable.

According to an embodiment, the final gas image 1100 is obtained by adjusting pixel values of an LP image 701 according to a predetermined palette of pixel values, wherein the predetermined palette comprises a selection of the palette options presented above.

According to an embodiment, generating a third image comprises combining a generated difference image 400, 600 or LP image 701 with an image 1200 depicting the scene. According to an embodiment, the combination comprises adjusting pixel values in an image 1200 depicting the scene, dependent on a generated difference image 400, 600 or LP image 701, for instance by adding the difference or LP image to, or multiplying the difference or LP image with, the image depicting the scene.

As described above in connection with step 416, the difference image 400, 600 or LP image 701 may according to embodiments further have been adjusted according to a predetermined color or grey scale palette before it is added to the image depicting the scene. According to an embodiment, the difference image 400, 600 or LP image 701 may be multiplied by a factor, e.g. between 0 and 1, before it is added to, or multiplied with, the image depicting the scene, thereby adding information according to an opacity determined by said factor.

According to an embodiment, the pixel values of the LP image 701 have been adjusted in step 416 in order to obtain an intermediate gas image with adjusted pixel values 1000, and wherein said intermediate gas image with adjusted pixel values 1000 is combined with an image depicting a scene in step 418.

According to an embodiment, gas detection has been performed in an LP image 701 in step 412 thereby generating a gas map 800, where after the generated gas map may be used as input into further method steps, comprising any or all of the optional steps 414 to 418, according to embodiments described above.

According to an embodiment, the final gas image 1100 is obtained by combining a selected image depicting the scene 1200 with the intermediate gas image 900 or the adjusted intermediate gas image 1000 in such a way that the pixel values of the pixels in the image depicting the scene 1200 corresponding to the gas representing pixels are adjusted based on the pixel values of the pixels in the intermediate gas image 900 corresponding to the gas representing pixels. Thereby a resulting final gas image 1100 is generated, wherein the depicted scene and gas present in the depicted scene is visualized, and wherein the location relation between the scene and gas present in the scene is substantially accurate. In other words, the intermediate gas image 900 is combined with an image depicting the scene 1200, to generate a final gas image 1100 wherein gas present in the depicted scene is visualized. Alternatively, if the optional step 416 has been performed, the adjusted intermediate gas image 1000 is combined with an image depicting the scene 1200, to generate a final gas image 1100 wherein gas present in the depicted scene is visualized.

There are several further different options and embodiments in the generation of the final gas image 1000. The final gas image may for example be based on:
- The adjusted intermediate gas image 1000 according to different palettes;
- The intermediate image only comprising the difference image; and/or
- Generating a cloud structure substantially covering the gas pixels.

A cloud structure may be fitted onto the gas pixels or more approximately covering the gas pixels, for example oriented around the center of detected gas pixels. Such a cloud structure may be a predefined item such as a clip-art cloud stored in memory, and may be superimposed on the final gas image. The cloud structure may be scalable or have a standardized size.

Options for Basic Image for Gas Visualization Image

According to embodiments, the image 1200 depicting the scene and being used as a basis for the gas visualization image can be selected from various options. In one embodiment the image 1200 is an IR image and the final gas image 1100 is generated by adjusting the pixel values of gas representing pixels in the IR image 1200, wherein the IR image 1200 is either the first IR image 100, the second IR image 200, or a third, different, IR image, depicting the scene, captured using the same IR imaging system that was used for capture of the first and second IR images, the IR imaging system being comprised in the IR imaging device, such as an IR camera or IR imaging arrangement.

According to another embodiment, the image 1200, depicting the scene, is generated from a temporal difference image 400 or the processed difference image 600, similarly adjusting the pixel values of pixels corresponding to the detected gas representing pixels.

According to other embodiments, the final gas image 1100 is generated by adjusting the pixel values of gas representing pixels in an image 1200, depicting the scene, wherein the image 1200 has been captured using a different IR imaging system, a visible light imaging system, or any other kind of imaging system adapted to receiving a certain range of wavelengths of light and generating a visible representation of said received light, comprised in or communicatively coupled to the IR imaging device, such as an IR camera, or IR imaging arrangement.

According to another embodiment, the image 1200, depicting the scene, is a fused image, the fused image being a result of a fusion between an IR image depicting the scene and a visible light image, also referred to as a visual image, depicting the same scene. The fused IR image and visible light image used have been captured using an IR imaging system and a visible light imaging system, respectively, the imaging systems for instance being comprised in the IR imaging device, such as an IR camera, or IR imaging arrangement or communicatively coupled to the IR imaging device, such as an IR camera, or IR imaging arrangement. According to this embodiment, the final gas image 1100 is generated by adjusting the pixel values of gas representing pixels in the fused image. Fusion of an IR image and a visual light image may be performed in any method per se known in the art and is not further described herein.

An example of a final gas image 1100 is shown in FIG. 2D. As shown in FIG. 2D, gas present in the scene is distinguishably visualized in the final gas image 1100, thereby making it easy for a person viewing the final gas image 1100 to interpret the image and visually detect whether there is gas present in the scene and, if that is the case, how much gas there is and where in the scene the gas is located. In other words, an easily interpretable visualization of gas is provided.

Gas Visualization Options

According to an embodiment, each pixel comprising detected gas is represented as 3 bits of information, wherein one bit of information comprises color information. The color information may for instance span from different saturation levels of green for negative values to different saturation levels of red for positive values. For instance, the color values may have a range of −1 to 1, wherein −1 is equal to fully saturated green, 0 is equal to no color/no saturation, and 1 is equal to fully saturated red. According to this embodiment, the second and third bits of information in each pixel comprise the pixel values of the original grey scale image. In other words, the pixel values of the original image are not over-written, but kept in their original form, simply adding one bit of color information. In this way, the "gas cloud look" is kept, since the gas is visualized in a transparent manner, the added color information having varying opacity. This further improves the interpretability of the gas information visualized in the image, since the partially transparent cloud, or plume, visualized in the image is very intuitively interpreted as gas.

As is readily apparent to a person skilled in the art, any suitable numerical or other scale may be used to describe the range of the bit information, and any selection of color values, such as hue and saturation, light/intensity and/or grey scale values may be used to visualize the bit information.

According to another embodiment each pixel is represented as a three bit color using any known color space representation, for instance RGB, CIEXYZ or CIELab.

Alignment

If an IR image captured using the same IR imaging system as is used for capturing the first and second IR images is used as a basis for the final gas image 1100, there is naturally no parallax between different imaging systems. Thereby, there will be no parallax related pixel displacements that need to be compensated for when combining the image information in the intermediate gas image with adjusted pixel values 1000, or the intermediate gas image 900, with the IR image used as a basis for the final gas image 1100.

According to the embodiments wherein different imaging systems, such as for instance two different IR imaging systems or an IR imaging system and a visual imaging system, are used to capture image information, the optical axes between the imaging components may be at a distance from each other and an optical phenomenon known as parallax will arise, causing parallax related pixel displacement between the images captured with different imaging systems. To eliminate the parallax related errors, arising from the parallax distance between the imaging systems and an angle between the optical axes of the imaging systems, the images that are to be combined in some way must first be aligned.

Therefore, after capture, the visual image and the IR image may be aligned to compensate for the parallax between the optical axes that generally arises due to differences in placement of the sensors for capturing said images and the angle created between these axes because of mechanical tolerances that generally prevents them being mounted exactly in parallel.

Computer Readable Medium

According to an embodiment of the invention, there is provided a computer-readable medium on which is stored non-transitory information for performing a method comprising capturing a first IR image depicting the scene at a first time instance; capturing a second IR image depicting the scene at a second time instance; performing image processing operations on image data derived from the first and second IR images to generate a collection of data representing the location of gas in one of the first or second IR image; detecting gas within the scene by detecting gas representing pixels in the first or second IR image of the previous step based on the collection of data; and generating a gas visualizing image by adjusting, in an image depicting the scene, pixel values of pixels corresponding to the gas representing pixels in the first or second IR image of the previous step, such that the gas representing pixels are distinguishable in the gas visualizing image.

According to further embodiments, there is provided computer-readable mediums on which is stored non-transitory information for performing any of the method embodiments described above.

System Architecture

Figure 6:
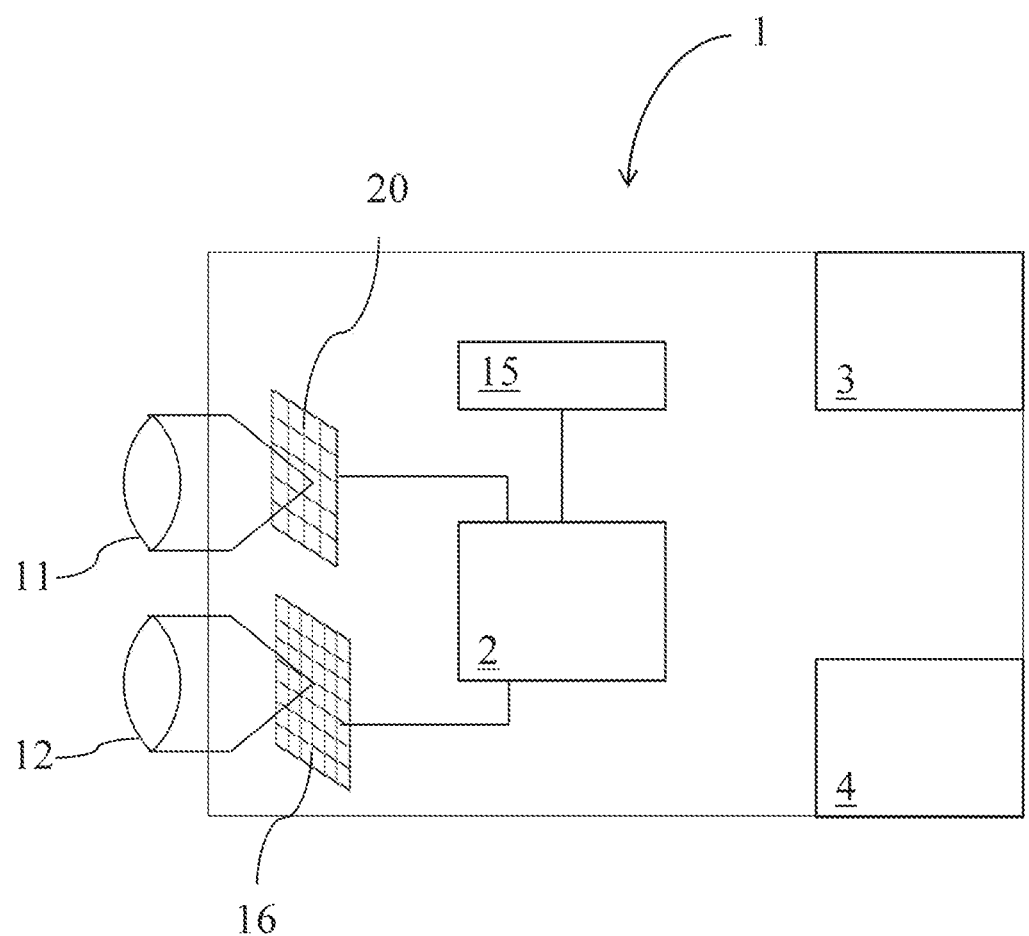
FIG. 6 shows a schematic view of an IR imaging system, in accordance with an embodiment of the invention.

FIG. 6 shows a schematic view of an embodiment of an IR imaging device or IR imaging arrangement 1 that comprises an IR imaging system 12 having an IR sensor 20.

According to an embodiment, an IR imaging device is realized as a device wherein the units and functionality for performing, capturing, and processing of images are integrated in the device. An IR imaging device may for instance be realized as an IR camera. According to an embodiment, an IR imaging arrangement comprises one or more units and enables communication and/or transfer of data between the comprised one or more units for performing, capturing, and processing of images. Hereinafter, in the description of the system architecture, the terms IR imaging device and IR imaging arrangement will be used interchangeably, wherein the only difference lies in whether the units and functionality are comprised in a single physical unit or device, or whether the units and functionality are communicatively or otherwise coupled, thereby constituting an arrangement of one or more physical units or devices.

According to embodiments, the IR imaging device or arrangement 1 may further comprise a visible light imaging system 11 having a visual sensor 16. The IR imaging device or arrangement 1 further comprises at least one memory 15.

The capturing of IR images is performed by IR imaging system 12 comprised in the IR imaging device or arrangement 1. Optionally, also visual images are captured by a visible light imaging system 11 comprised in the IR imaging device or arrangement 1. The captured one or more images are transmitted to a processing unit 2 capable of performing image processing operations, comprised in the IR imaging device 1. The captured images may also be transmitted with possible intermediate storing to a processing unit comprised in the IR imaging arrangement 1 and being coupled to, but physically separate or external from, the imaging systems 12, 11. According to an embodiment, the processing unit is configured to receive and process infrared image data from the IR imaging system 12. The processing integrated in the IR imaging device or the separate processing unit coupled to the IR arrangement are provided with specifically designed programming or program code portions adapted to control the processing unit to perform the steps and functions of embodiments of the inventive method described herein.

The processing unit 2 may be a processor such as a general or special purpose processing engine for example a microprocessor, microcontroller or other control logic that comprises sections of code or code portions, stored on a computer readable storage medium, that are fixed to perform certain tasks but also other sections of code, stored on a computer readable storage medium, that can be altered during use. Such alterable sections can comprise parameters that are to be used as input for the various tasks, such as the calibration of the imaging device or arrangement 1, the sample rate or the filter for the spatial filtering of the images, among others.

According to an embodiment, the processor or processing unit 2 is configured to process infrared image data from the infrared sensor depicting a scene. According to further embodiment, the processor is configured to receive a first IR image depicting the scene and being captured at a first time instance; receive a second IR image depicting the scene and being captured at a second time instance; perform image processing operations on image data derived from the first and second IR images to generate a collection of data representing the location of gas in the image; and generate a third image, e.g. being a gas visualizing image, by adjusting pixel values, in an image depicting the scene, dependent on the collection of data.

According to an embodiment, the processing unit 2 is configured to generate a third image, or gas visualization image, by adjusting pixel values, in an image depicting the scene, dependent on the collection of data. According to an embodiment, the processing unit 2 is configured to generate a third image, or gas visualization image, by adjusting pixel values of pixels corresponding to gas representing pixels in the first or second captured IR image, such that the gas representing pixels are distinguishable in the gas visualizing image.

According to an embodiment, the processing unit 2 is configured to detect gas within the scene by detecting gas representing pixels in the first or second IR image based on the collection of data.

According to one or more embodiments of the present invention, the processing unit 2 is configured to perform the steps according to any or all of the method embodiments presented herein. According to an embodiment, the processing unit 2 is configurable using a hardware description language (HDL).

According to an embodiment, the processing unit 2 is a Field-programmable gate array (FPGA), i.e. an integrated circuit designed to be configured by the customer or designer after manufacturing. For this purpose embodiments of the invention comprise configuration data configured to control an FPGA to perform the steps and functions of the method embodiments described herein.

In this document, the terms "computer program product" and "computer-readable storage medium" may be used generally to refer to media such as a memory 15 or the storage medium of processing unit 2 or an external storage medium. These and other forms of computer-readable storage media may be used to provide instructions to processing unit 2 for execution. Such instructions, generally referred to as "computer program code" (which may be grouped in the form of computer programs or other groupings), when executed, enable the IR camera 1 to perform features or functions of embodiments of the current technology. Further, as used herein, "logic" may include hardware, software, firmware, or a combination of thereof.

The processing unit 2 communicates with a memory 15 where parameters are kept ready for use by the processing unit 2, and where the images being processed by the processing unit 2 can be stored if the user desires. The one or more memories 15 may comprise a selection of a hard disk drive, a floppy disk drive, a magnetic tape drive, an optical disk drive, a CD or DVD drive (R or RW), or other removable or fixed media drive.

Further Embodiments

According to an embodiment, the user can save the final gas image 1100 or any of the previous images corresponding to the different method steps to the memory 15 for later viewing or for transfer to another unit, such as a computer, for further analysis and storage.

In an alternative embodiment, disclosed methods can be implemented by a computing device such as a PC that may encompass the functions of an FPGA-unit specially adapted for performing the steps of the method for one or more embodiments of the present invention, or encompass a general processing unit 2 according to the description in connection with FIG. 6. The computing device may be a part of an IR imaging arrangement 1 and be communicatively or otherwise coupled to the units and functionality of the IR imaging arrangement 1. The computing device may further comprise the memory 15 and also the display unit 3. It would be possible to use the disclosed methods live, i.e. for a streamed set of images filtered and combined in real time, or near real time, for instance at 30 Hz, that can be recorded and replayed as a movie, but it would also be possible to use still pictures.

According to an embodiment the IR camera comprises a visual imaging device and the processor 2 is adapted to perform fusion. According to this embodiment, the image depicting the scene 1200, which is combined with an intermediate gas image 900 or an intermediate gas image with adjusted pixel values 1000 to generate a final gas image 1100, may be a visual image may be used as. Alternatively, the detected gas may be added to and colored in a visual image and an IR image, respectively.

According to an embodiment, the final gas image 1100 comprising a visualization of gas present in the scene is presented to the user of the IR camera on a display 3 comprised in, or communicatively coupled to, the IR camera.

According to an embodiment, the processing unit 2 is adapted to perform image processing operations on image data derived from the first and second IR images to generate a collection of data representing the location of gas in the image.

According to an embodiment, the processing unit 2 is adapted to detect gas within the scene by detecting gas representing pixels in the first or second IR image of the previous step based on the collection of data.

According to an embodiment, the processing unit 2 is adapted to generate a gas visualizing image, also referred to as a final gas image 1100, by adjusting, in an image 1200 depicting the scene, pixel values of pixels corresponding to gas representing pixels in the first or second IR image of the previous step, such that the gas representing pixels are distinguishable in the gas visualizing image.

According to an embodiment, the IR imaging device or arrangement 1 further comprises interaction functionality 4, enabling the operator of the IR imaging device or arrangement 1 to provide input to the IR imaging device or arrangement. According to an embodiment, the interaction functionality comprises a selection of one or more control devices for inputting commands and/or control signals, e.g. an interactive display, joystick and/or record/push-buttons.

According to an embodiment, the operator may adjust the sensitivity of the gas detection with relation to how much of the gas present in the scene that is to be detected versus how much noise in the image that will be wrongfully interpreted as gas and detected by the gas detection method.

According to an embodiment, the sensitivity level value is a function of the two thresholds of the optional edge detection steps S520 and S540, and the threshold of the gas detection step 412. Thereby, the adjustment of the combined sensitivity value will lead to adjustments of all thresholds, according to a predetermined function.

According to another embodiment, one or more of the thresholds for steps 414, S520 and S540 may be adjusted separately, or in combination.

An increased threshold value for steps S520 and S540 leads to a less sensitive detection, possibly allowing more gas information to be interpreted as edges and thereby removed, while an increase of the threshold value for step 412 leads to a more sensitive detection wherein pixels with pixel values within a larger range are detected as comprising gas information.

Thereby, if the operator wants to be sure that no gas information is missed in the detection, the sensitivity may be manually decreased, while if the operator wants to be sure not to include anything but gas in the detection result, the sensitivity may be manually increased. The operator may further adjust the gas sensitivity up and down, viewing the result on the display 3 of the IR imaging device or arrangement 1, until the operator is satisfied with the displayed result.

Use Case

In an exemplifying use case of an embodiment, an operator of an IR imaging device 1 aims the IR imaging device at target scene, wherein presence of gas, for example gas leaking from a pipe, is suspected.

While aiming the IR imaging device 1 at the target scene, the operator is presented with an image wherein any gas present in the scene is visualized, in real time or near real time, on a display 3 of the IR imaging device 1. Any gas present in the scene is detected and visualized for every image frame in the sequence of image frames that is captured by the IR imaging device 1. Since the detected gas is visualized for every frame, the operator viewing the displayed image sequence on the display 3 of the IR imaging device 1 will see a moving visualization of gas, wherein the visualized gas is correctly located in relation to the rest of the scene in real time. This is enabled by visualizing gas onto, or approximately onto, the pixels in the image where gas information has been detected.

According to embodiments of the invention the visualized gas has correct size and distribution, since it is visualized onto the pixels that have been identified as comprising gas information.

According to embodiments of the invention the visualized gas has a gas-like, or cloud-like, appearance, for instance by the gas information being superimposed onto the image depicting the scene in a non-opaque manner and/or by the gas information being colored using more than one color hues and/or saturation levels. Furthermore, since the gas visualization is updated for every frame and correctly or at least nearly correctly depicts the shape of the detected gas, the operator will experience that the visualized gas moves continuously in a gas-like manner as the visualization changes from frame to frame.

Further Advantages

The method according to the inventive embodiments improves the gas detection and visualization performance of any type of IR camera, whether it is a camera with cooled detectors or with uncooled detectors, since the method makes the detection more accurate due to the fact that smaller differences in the IR images will be made distinguishable.

For uncooled detector cameras it is typically hard to distinguish a difference between data of different wavelengths. Furthermore, the images often comprise a lot of noise. The image processing steps of the inventive method thereby enable gas detection in such images, where it was not previously possible.

For cooled detector cameras, the gas detection and visualization performance is improved compared to previous methods.

As can be readily understood by a person skilled in the art, if the IR camera used is adapted to a certain wide or narrow band of wavelength radiation it will still obtain the advantageous gas detection and visualization capabilities.

According to an embodiment, the IR camera may be a single band IR camera, meaning that the IR camera is adapted to receiving radiation within a certain range of wavelengths and creating images showing a visible representation of said received radiation. This adaptation of the IR camera, i.e. fixed wavelength range sensitivity, may be accomplished either by the use of fixed optical elements between the depicted scene and the IR sensor 20, or by adjustable physical/hardware or software optical elements, such as for instance dual band filters or filter wheels, that are temporarily fixed. To temporarily fixate the optical elements would result in the IR camera working as a single band IR camera, i.e. an IR camera with fixed wavelength range sensitivity.

According to another embodiment, the IR camera may be a single band IR camera, meaning that the IR camera imaging systems are adapted to receiving radiation within a certain range of wavelengths and creating images showing a visible representation of said received radiation.

Some examples of gases that may be of interest to detect and visualize are: 1-Pentene, Benzene, Butane, Ethane, Ethanol, Ethyl benzene, Ethylene, Heptane, Hexane, Isoprene, MEK, Methane, Methanol, MIBK, Octane, Pentane, Propane, Propylene, Toluene and/or Xylene.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method for gas detection in an infrared (IR) image depicting a scene, the method comprising:
 receiving a first IR image depicting the scene captured at a first time instance and receiving a second IR image depicting the scene captured at a second time instance;
 performing image processing operations on image data derived from the first IR image and from the second IR image, to generate a collection of data representing the location of gas in the first IR image;
 wherein the image processing operations include:
  generating a temporal difference image based on the first IR image and the second IR image,
  low-pass filtering the generated temporal difference image, and
  generating a processed difference image as part of the collection of data by adding the low-pass filtered temporal difference image to, or by multiplying the low-pass filtered temporal difference image with, the first IR image; and
 detecting gas within the scene by detecting gas representing pixels and identifying pixel coordinates of the gas representing pixels based on thresholding of the processed difference image.

2. The method of claim 1, wherein the image processing operations further comprise processing of the processed difference image before thresholding of the processed difference image, the processing of the processed difference image comprising transforming the processed difference image into the frequency domain by an FFT operation or a PSD operation, wherein the detecting of the gas representing pixels and identifying pixel coordinates of the gas representing pixels is based on thresholding of the transformed and processed difference image.

3. The method of claim 2, wherein the transforming of the processed difference image into the frequency domain is performed block wise, using image blocks of a size smaller than the size of the difference image, and/or as a sub-portion of the pixels of the difference image, thereby resulting in a down-sampled frequency domain image.

4. The method of claim 1, further comprising, after the detecting of the gas within the scene, generating a third image by adjusting, in an image depicting the scene, pixel values of pixels that correspond to the gas representing pixels such that the gas representing pixels are distinguishable.

5. The method of claim 4, wherein the generation of the third image comprises creating a gas map comprising detected gas representing pixels in the form of a binary gas image.

6. The method of claim 5, wherein the generation of the third image further comprises:
 adjusting, in an image depicting the scene, pixel values of pixels corresponding to the detected gas representing pixels, the image having a predetermined relation to the first and second IR images;
 adjusting, in the processed difference image, pixel values of pixels corresponding to the detected gas representing pixels; and/or
 combining the gas map with the processed difference image such that pixels corresponding to pixels that have been identified as representing gas information in the gas map are assigned the pixel values of the corresponding pixels in the difference image, to generate an intermediate gas image.

7. The method of claim 1, further comprising:
 performing edge detection in at least one of the first and the second IR image to provide detected edge information;
 creating an edge map comprising the detected edge information, wherein the pixels representing the detected edge information are assigned a first pixel value and the remaining pixels are assigned a second pixel value; and combining the edge map with the generated temporal difference image such that the detected edge information is removed before the temporal difference image is low-pass filtered.

8. The method of claim 7, wherein the edge map is in the form of a binary edge image and where combining of the edge map with the generated temporal difference image further comprises a selection of:
  subtracting the binary image from the generated temporal difference image; or
  multiplying the binary image with the generated temporal difference image.

9. An infrared (IR) imaging arrangement for gas detection in an IR image depicting a scene, the IR imaging arrangement comprising:
  an IR sensor configured to capture IR image data depicting a scene;
  a processor configured to receive and process IR image data from the IR sensor, the processor being further configured to:
    receive a first IR image depicting the scene and captured at a first time instance;
    receive a second IR image depicting the scene and captured at a second time instance;
    perform image processing operations on image data derived from the first and the second IR images to generate a collection of data representing the location of gas in the first IR image, wherein the image processing operations comprise:
      generating a temporal difference image based on the first IR image and the second IR image,
      low-pass filtering the generated temporal difference image, and
      generating a processed difference image as part of the collection of data by adding the low-pass filtered temporal difference image to, or by multiplying the low-pass filtered temporal difference image with, the first IR image; and
    detect gas within the scene by detecting gas representing pixels and identifying pixel coordinates of the gas representing pixels based on thresholding of the processed difference image.

10. The infrared (IR) imaging arrangement of claim 9, further comprising a visible light imaging sensor configured to capture a visual light image depicting the scene and having a predetermined relation to the first and the second IR images, wherein the processor is coupled to the IR sensor.

11. The IR imaging arrangement of claim 9, wherein the processor is a field-programmable gate array (FPGA).

12. The IR imaging arrangement of claim 9, wherein the image processing operations further comprise processing of the processed difference image before thresholding of the processed difference image, the processing of the processed difference image comprising transforming the processed difference image into the frequency domain by an FFT operation or a PSD operation, wherein the processor is further configured to detect the gas representing pixels and identify pixel coordinates of the gas representing pixels based on thresholding of the transformed and processed difference image.

13. A computing system configured to process infrared (IR) image data for gas detection in an IR image depicting a scene, the computing system comprising:
  a memory configured to store infrared image data depicting a scene;
  a processor configured to process infrared image data stored in the memory, the processor being further configured to:
    receive from the memory a first IR image depicting the scene captured at a first time instance;
    receive from the memory a second IR image depicting the scene captured at a second time instance;
    perform image processing operations on image data derived from the first and the second IR images to generate a collection of data representing the location of gas in the first IR image, wherein image processing operations comprise:
      generating a temporal difference image based on the first IR image and the second IR image,
      low-pass filtering the generated temporal difference image, and
      generating a processed difference image as part of the collection of data by adding the low-pass filtered temporal difference image to, or by multiplying the low-pass filtered temporal difference image with, the first IR image; and
    detect gas within the scene by detecting gas representing pixels and identifying pixel coordinates of the gas representing pixels based on thresholding of the processed difference image.

14. The computing system of claim 13, wherein the processor is a field-programmable gate array.

15. The computing system of claim 13, wherein the image processing operations further comprise processing of the processed difference image before thresholding of the processed difference image, the processing of the processed difference image comprising transforming the processed difference image into the frequency domain by an FFT operation or a PSD operation, wherein the processor is further configured to detect the gas representing pixels based on thresholding the transformed and processed difference image.

16. The computing system of claim 13, wherein the system further comprises an IR sensor configured to capture the infrared image data depicting the scene, wherein the processor is configured to receive and process the IR image data from the IR sensor.

17. The computing system of claim 13, wherein the processor is configured to generate a collection of data at least by creating a gas map comprising detected gas representing pixels in the form of a binary gas image.

18. The computing system of claim 17, wherein the processor is configured to generate a third image by adjusting, in an image depicting the scene, pixel values of pixels that correspond to the gas representing pixels such that the gas representing pixels are distinguishable, the adjusting comprising:
  adjusting, in an image depicting the scene, pixel values of pixels corresponding to the detected gas representing pixels, the image having a predetermined relation to the first and second IR images; and/or
  combining the gas map with the processed difference image such that pixels corresponding to the pixels that have been identified as representing gas information in the gas map are assigned the pixel values of the corresponding pixels in the difference image, to generate an intermediate gas image.

19. The computing system of claim 13, further comprising:
  performing edge detection in at least one of the first and the second IR image;

creating an edge map comprising the detected edge information, wherein the pixels representing detected edge information are assigned a first pixel value and the remaining pixels are assigned a second pixel value; and combining the edge map with the generated temporal difference image before this is low-pass filtered.

20. The computing system of claim 19, wherein the edge map is in the form of a binary edge image, and wherein the generating of the processed difference image further comprises a selection of:

subtracting the binary image from the processed difference image; or multiplying the binary image with the processed difference image.

* * * * *

UNITED STATES PATENT AND TRADEMARK OFFICE
CERTIFICATE OF CORRECTION

PATENT NO. : 9,984,447 B2
APPLICATION NO. : 15/468044
DATED : May 29, 2018
INVENTOR(S) : Katrin Strandemar Page 1 of 1

It is certified that error appears in the above-identified patent and that said Letters Patent is hereby corrected as shown below:

In the Specification

In the Detailed Description:

In Column 8, Line 52, change "skilled in the aft" to --skilled in the art--.

In Column 14, Line 45, change "skilled in the aft" to --skilled in the art--.

In Column 18, Line 4, change "goo, such that" to --900, such that--.

In Column 18, Line 11, change "image goo" to --image 900--.

In Column 25, Line 18, change "in the aft" to --in the art--.

Signed and Sealed this
Tenth Day of July, 2018

Andrei Iancu
*Director of the United States Patent and Trademark Office*